United States Patent
Guillen-Portal

(10) Patent No.: US 8,319,021 B2
(45) Date of Patent: Nov. 27, 2012

(54) CAMELINA SATIVA VARIETY 'SO-50'

(75) Inventor: Fernando Guillen-Portal, Bozeman, MT (US)

(73) Assignee: Targeted Growth, Inc., Seattle, WA (US)

( * ) Notice: Subject to any disclaimer, the term of this patent is extended or adjusted under 35 U.S.C. 154(b) by 193 days.

(21) Appl. No.: 12/945,438

(22) Filed: Nov. 12, 2010

(65) Prior Publication Data

US 2012/0124693 A1    May 17, 2012

(51) Int. Cl.
*A01H 5/00* (2006.01)
*A01H 5/10* (2006.01)
*A01H 1/00* (2006.01)
*C12N 15/82* (2006.01)

(52) U.S. Cl. .................. 800/306; 800/260; 435/430

(58) Field of Classification Search .................. None
See application file for complete search history.

(56) References Cited

U.S. PATENT DOCUMENTS

2012/0124692 A1 * 5/2012 Guillen-Portal .............. 800/265

OTHER PUBLICATIONS

Pilgeram et al., "*Camelina sativa*, A Montana Omega-3 and Fuel Crop", Reprinted from: Issues in new crops and new uses. 2007. J. Janick and A. Whipkey (eds.). ASHS Press, Alexandria, VA.
Lu et al., "*Camelina sativa:* A Potential Oilseed Crop for Biofuels and Genetically Engineered Products", ISB News Report, Jan. 2008.
Vollmann et al., "Improvement of *Camelina sativa*, an Underexploited Oilseed", 1996, In: J. Janick (ed.), Progress in new crops. ASHS Press, Alexandria, VA. p. 357-362.
Gugel et al., "Agronomic and seed quality evaluation of *Camelina sativa* in western Canada", Canadian Journal of Plant Science; 2006, 86:1047-1058.
U.S. Appl. No. 12/945,455, Fernando Guillen-Portal.
U.S. Appl. No. 12/945,420, Fernando Guillen-Portal.

* cited by examiner

*Primary Examiner* — Elizabeth McElwain
(74) *Attorney, Agent, or Firm* — Cooley LLP

(57) ABSTRACT

The invention relates to a *Camelina sativa* (L.) Crantz spring-type seed designated as 'SO-50' derived from a cross between *camelina* accessions with high yield and oil quality attributes following conventional breeding methodologies.

20 Claims, No Drawings

CAMELINA SATIVA VARIETY 'SO-50'

TECHNICAL FIELD

The invention relates to seed and any other plant material of a *Camelina sativa* (L.) Crantz variety named 'SO-50', which is a spring-type plant material with superior agronomic performance and broad adaptability to dryland, low-input agricultural systems in the USA. The seeds of the invention produce a significant large amount of seeds per plant, which constitute its major distinctive attribute.

BACKGROUND

Current trends in the international petroleum market and concerns on the excessive use of petroleum-derived fuels on the environment have led to increased interest in the development and adoption of renewable sources of energy in the USA. In some instances this has derived in the adoption of government policies, like the Energy Independency and Security Act of 2007 (Public Law 110-140, 2007), in others in the take-over of private initiatives like that aimed at using plant-derived renewable fuels to partly satisfy the fuel demand of the aviation industry (Anonymous, 2009).

Among the several types of feedstocks proposed for the production of renewable fuel, use of industrial-grade oilseed crops are considered a viable option. Camelina (*Camelina sativa*, (L.) Crantz), an annual plant that belongs to the Brassicaceae family, is an oilseed crop that can produce decent yields under relative low inputs, exhibits a broad adaptability to a range of environmental conditions, and its seeds contain a relatively high amount of oil (Putnam et al., 1993; Budin et al., 1995; Vollman et al., 1996; Gugel and Falk, 2006). In addition, studies on the impact of *camelina*-derived fuel on the environment indicates that use of this fuel can reduce carbon emissions by up to 80% (Shonnard et al., 2010) conferring this crop a potential to be used as biofuel feedstock crop.

Although *camelina* is a plant with a rich history (Schultze-Motel, J., 1979; Bouby, 1998), in general little genetic improvement has been practiced on this crop. In the USA, although efforts were devoted to this crop in the past (Porcher, 1863, Robinson, 1987), currently the number of varieties available for commercial production is very limited. Consequently, there is a real need to develop *camelina* varieties with high productivity and broad adaptability, especially to low-input agricultural systems in the USA, to be used as reliable, commercial feedstocks for the emerging biofuel industry.

The main object of the invention is to provide seed of a superior *camelina* variety that provides high and stable yields and is suitable of commercial production under low-input agricultural areas in the USA.

Another object is to provide seed of a *camelina* variety that exhibits acceptable and stable agronomic characteristics.

Furthermore, another object is to provide seed of a *camelina* variety that has the ability to produce a large number of seeds per plant.

Yet another object is to provide seed of a *camelina* variety with an average fatty acid composition.

SUMMARY OF THE INVENTION

The present invention provides *camelina* plants having increased grain yields and ability to grow efficiently and consistently under dryland, low-input conditions. In some embodiments, the *camelina* plant is a *Camelina sativa* (L.) variety. In some further embodiments, the *Camelina sativa* (L.) variety is the *camelina* plant designated as 'SO-50', a representative seed sample of which has been deposited under ATCC Accession No. PTA-11480 on Nov. 12, 2010. In some embodiments, the *camelina* plant is a plant having one or more, or all the physiological and morphological characteristics of *Camelina sativa* (L.) variety 'SO-50'. In some embodiments, the *camelina* plant is derived from a cross between a first parent *camelina* plant and a second parent *camelina* plant, wherein the first and/or the second *camelina* plants are *Camelina sativa* (L.) variety 'SO-50', or *camelina* plants having one or more, or all the physiological and morphological characteristics of *Camelina sativa* (L.) variety 'SO-50'.

The *camelina* plants of the present invention have higher yield compared to a check line. In some embodiments, the check line is 'Calena', 'Blaine Creek', 'Celine', 'Galena', 'Ligena', 'Robinson', or 'Suneson'. In some embodiments, said *camelina* plants are developed through conventional breeding methods, having the ability to grow efficiently and consistently under dryland, low-input conditions. The plants of the invented seed provide higher yields (e.g., about 1746 Lbs/ac) and are stable in their performance across a wide range of environmental conditions. In some embodiments, compared to a check line, the plants of the present invention are medium in maturity (e.g., about 106 days), mid-size in stature (e.g., about 33 inches), and produce a significant large amount of seed per plant (e.g., about 1989), one of its major distinctive attributes. In some embodiments, compared to a check line, the seeds of the *camelina* plants of the present invention contain an average amount of oil content (e.g., about 37.56%) and a high amount of oil yield (e.g., about 666 Lbs/ac).

The present invention also provides plant parts of the *camelina* plants of the present invention. In some embodiments, the plant part is the shoot, root, stem, seeds, racemes, stipules, leaves, petals, flowers, ovules, bracts, branches, petioles, internodes, pollen, stamen, or the like. In some embodiments, the plant part is the seed of the *camelina* plant designated as 'SO-50', a representative sample of which has been deposited under ATCC Accession No. PTA-11480 on Nov. 12, 2010.

The present invention also provides plant cells of the *camelina* plants of the present invention. In some embodiments, the plant cell can be cultured and use to produce a *camelina* plant having one or more, or all the physiological and morphological characteristics of the *camelina* plants of the present invention.

The present invention also provides tissue culture of the *camelina* plants of the present invention. In some embodiments, the tissue culture are produced from a plant part selected from the group consisting of embryos, meristematic cells, leaves, pollen, root, root tips, stems, anther, pistils, pods, flowers, and seeds. In some embodiments, the tissue culture can be used to regenerate a *Camelina sativa* (L.) plant, said plant having the morphological and physiological characteristics of *Camelina sativa* (L.) variety 'SO-50', wherein a representative sample of seed has been deposited under ATCC Accession No. PTA-11480 on Nov. 12, 2010.

The present invention also provides methods to produce the *camelina* plants of the present invention. In some embodiments, the plants are produced through conventional breeding methods.

The present invention further provides methods for producing a *Camelina* seed. In some embodiments, said methods comprise crossing a first parent *Camelina* plant with a second parent *Camelina* plant and harvesting the resultant hybrid bean seed, wherein said first parent *Camelina* plant or second parent *Camelina* plant is the *Camelina sativa* (L.) plant of the present invention. The present invention also provides methods for introducing one or more desired traits into *camelina* plants of the present application. In some embodiments, the methods comprise introducing one or more transgenes into the *camelina* plants of the present invention. In some other embodiments, the introducing step comprises crossing the *camelina* plants of the present invention to one or more transgenic plants, wherein the transgenic plants comprise one or more transgenes. In some embodiments, the transgene is a gene for herbicide resistance in a plant, and the herbicide is selected from the group consisting of imidazolinone, sulfonylurea, glyphosate, glufosinate, L-phosphinothricin, triazine, sethoxydim, and benzonitrile. In some embodiments, the transgene is a gene for insect resistance in a plant, for example, the transgene encodes a *Bacillus thuringiensis* endotoxin. In some embodiments, the transgene is a gene for disease resistant in a plant. In some embodiments, the transgene is a gene for water stress tolerance, heat tolerance, improved shelf life, and/or improved nutritional quality.

In some other embodiments, the methods comprise: (a) crossing a *camelina* plant of the present invention with another *camelina* plant that comprises a desired trait to produce F1 progeny plants; (b) selecting one or more progeny plants that have the desired trait to produce selected progeny plants; (c) crossing the selected progeny plants with the *camelina* plant of the present invention to produce backcross progeny plants; (d) selecting for backcross progeny plants that have the desired trait and physiological and morphological characteristics of the *camelina* plant of the present invention to produce selected backcross progeny plants; and (e) optionally, repeating steps (c) and (d) three or more times in succession to produce selected fourth or higher backcross progeny plants that comprise the desired trait and the physiological and morphological characteristics of the *camelina* plant of the present invention. In some embodiments, the desired trait is, for example, selected from the group consisting of insect resistance, disease resistance, water stress tolerance, heat tolerance, improved shelf life, and improved nutritional quality;

DETAILED DESCRIPTION OF THE INVENTION

Definitions

This document has been prepared using technical and scientific terms that are common to the field, thus, the term "Days to 50% flowering" refers to period from germination of the seed to the manifestation of flowering in 50% of the plant population.

"Days to Maturity" refers to the period from germination of the seed to the period when fully developed seeds where developed in 50% of the plant population.

"Seed filling days" refers to the period from the beginning of seed growth until the seed is fully developed and has reached maximum dry weight.

"Plant height" refers to the height of the adult plant from the ground base where it is being grown to the tip of the main raceme.

"Racemes per plant" refers to the number of reproductive branches derived from the main stem of the plant.

"Main raceme length" refers to the length of the terminal raceme in the plant.

"Inflorescence length" refers to the length of the main inflorescence from its base to the tip of the terminal raceme.

"Inflorescence diameter" refers to the diameter of the inflorescence at its widest plane and is measured right after flowering has been completed.

"Pod number" refers to the total number of pods in the plant bearing seeds.

"Pod weight" refers to the weight of a pod once the plant has reached maturity and consequently is ready to be harvested.

"Seeds per pod" refers to the number of fully developed seed contained inside a pod in the plant.

"Seeds per plant" refers to the total number of fully developed seeds the plant has produced.

"Seed weight" refers to the total weight of a fully developed seed, usually expressed in weight per thousand seeds.

"Test weight" refers to a measure of the seed weight in pounds for a given bushel volume.

"Grain yield" refers to a measure of the harvested clean seed weight in pounds in one acre of land area.

"Oil content" refers to the fraction of total oil contained in the mature seed.

"Oil yield" refers to a measure of the seed oil weight collected in pounds in one acre of land area.

"Variety" refers to a homogeneous, highly homozygous group of individuals that are genetically distinct from other groups of individuals within the species.

"Cross" refers to the process by which pollen from one flower from a plant is artificially transferred to the stigma from the flower of another plant.

"Progeny" refers to the offspring derived from an artificial cross between two plants.

"Selfing" refers to the manifestation of the process of self-pollination, which in turn refers to the transfer of pollen from the anther of a flower to the stigma of the same flower or different flowers on the same plant.

"Single plant selection" refers to a form of selection in which plants with specific desirable attributes are identified and individually selected.

"Seed increase" refers to the process of sowing, growing and harvesting seed from a specific plant material for the purpose of creating a larger volume of seed.

As used herein, the verb "comprise" as is used in this description and in the claims and its conjugations are used in its non-limiting sense to mean that items following the word are included, but items not specifically mentioned are not excluded.

As used herein, the term "plant" refers to any living organism belonging to the kingdom Plantae (i.e., any genus/species in the Plant Kingdom). For example, the plant is a species in the tribe of Camelineae, such as *C. alyssum, C. anomala, C. grandiflora, C. hispida, C. laxa, C. microcarpa, C. microphylla, C. persistens, C. rumelica, C. sativa, C. Stiefelhagenii*, or any hybrid thereof.

As used herein, the term "plant part" refers to any part of a plant including but not limited to the shoot, root, stem, seeds, racemes, stipules, leaves, petals flowers, ovules, bracts, branches, petioles, internodes, tiller, pollen, stamen, and the like. The two main parts of plants grown in some sort of media, such as soil, are often referred to as the "above-ground" part, also often referred to as the "shoots", and the "below-ground" part, also often referred to as the "roots".

The term "a" or "an" refers to one or more of that entity; for example, "a gene" refers to one or more genes or at least one gene. As such, the terms "a" (or "an"), "one or more" and "at least one" are used interchangeably herein. In addition, reference to "an element" by the indefinite article "a" or "an" does not exclude the possibility that more than one of the elements are present, unless the context clearly requires that there is one and only one of the elements.

As used herein, the term "cross", "crossing", "cross pollination" or "cross-breeding" refer to the process by which the pollen of one flower on one plant is applied (artificially or naturally) to the ovule (stigma) of a flower on another plant.

As used herein, the term "gene" refers to any segment of DNA associated with a biological function. Thus, genes include, but are not limited to, coding sequences and/or the regulatory sequences required for their expression. Genes can also include nonexpressed DNA segments that, for example, form recognition sequences for other proteins. Genes can be obtained from a variety of sources, including cloning from a source of interest or synthesizing from known or predicted sequence information, and may include sequences designed to have desired parameters.

Camelina sativa

*Camelina sativa*, usually known in English as *camelina*, gold-of-pleasure, or false flax, also occasionally wild flax, linseed dodder, German sesame, and Siberian oilseed, is a flowering plant in the family Brassicaceae which includes mustard, cabbage, rapeseed, broccoli, cauliflower, kale, brussels sprouts. It is native to Northern Europe and to Central Asian areas, but has been introduced to North America, possibly as a weed in flax.

The crop is now being researched due to its exceptionally high levels (up to 45%) of omega-3 fatty acids, which is uncommon in vegetable sources. *Camelina* has a fatty acid composition with high levels of both polyunsaturated fatty acids such as 18:2 and 18:3 (52-54%) as well as long chain fatty acids such as 20:1 (11-15%) and 22:1 (2-5%). Over 50% of the fatty acids in cold pressed *camelina* oil are polyunsaturated. The major components are alpha-linolenic acid—C18:3 (omega-3-fatty acid, approx 35-45%) and linoleic acid—C18:2 (omega-6 fatty acid, approx 15-20%). The oil is also very rich in natural antioxidants, such as tocopherols, making this highly stable oil very resistant to oxidation and rancidity. It has 1-3% erucic acid. The vitamin E content of *camelina* oil is approximately 110 mg/100 g. It is well suited for use as a cooking oil. It has an almond-like flavor and aroma. It may become more commonly known and become an important food oil for the future (Pilgeram et al., 2007, *Camelina sativa*, A Montana Omega-3 and Fuel Crop, Issues in new crops and new use; Vollmann et al., Improvement of *Camelina sativa*, an Underexploited Oilseed; Putnam et al., *Camelina*: A Promising Low-input Oilseed; Berti and Schneiter, Preliminary Agronomic Evaluation of New Crops for North Dakota; Pavlista and Baltensperger, Phenology of Oilseed Crops for Bio-Diesel in the High Plains, each of which is incorporated by reference in its entirety).

*Camelina* can be used for as commercial feed (US FDA clarification to states, Currently allowed practices for use of *Camelina sativa* meal as a commercial feed in Montana, September 2010). *Camelina* also produce useful chemicals, for example, camalexins (Browne et al., Tetrahedron, Volume 47, Issue 24, 1991, Pages 3909-3914).

Methods of transforming *camelina* plant have been described in US20040031076, US20090151028, US20090151023, WO/2002/038779A1, and WO/2009/117555A1, each of which is incorporated by reference in its entirety.

Methods for *camelina* tissue culture have been described previously. For example, *Camelina sativa* shoots have been regenerated from leaf explants (Tattersall and Millam, Plant Cell Tissue and Organ Culture 55:147-149, 1999). *Camelina sativa* has also been used in a somatic fusion with other *Brassica* species (Narasimhulu et al., Plant Cell Rep. 13:657-660, 1994; Hansen, Crucifer. News 19:55-56, 1997; Sigareva and Earle, Theor. Appl. Genet. 98:164-170, 1999) and regenerated interspecific hybrid plants were obtained (Sigareva and Earle, Theor. Appl. Genet. 98:164-170, 1999). More tissue culture techniques for *Camelina* can be found in Bhojwani and Razdan (Plant tissue culture: theory and practice, Elsevier, 1996, ISBN 97804448162328), Trigiano and Gray (Plant tissue culture concepts and laboratory exercises, Volume 1999, CRC Press, 2000, ISBN 0849320291, 9780849320293), Kumar (Plant Tissue Culture And Molecular Markers: Their Role In Improving Crop Productivity, I. K. International Pvt Ltd, 2009, ISBN 8189866109, 9788189866105), George et al., (Plant Propagation by Tissue Culture 3rd Edition: Volume 1. the Background, ISBN 1402050046, 9781402050046). Sathyanarayana (Plant Tissue Culture: Practices and New Experimental Protocols, I. K. International Pvt Ltd, 2007, ISBN 8189866117, 9788189866112), Pierik (In vitro culture of higher plants, Springer, 1997, ISBN 0792345274, 9780792345275), and Vasil (Plant cell and tissue culture, Springer, 1994, ISBN 0792324935, 9780792324935), each of which is incorporated by reference in its entirety herein for all purposes.

Camelina sativa (L.) Variety 'SO-50'

*Camelina sativa* (L.) variety 'SO-50' is a true-bred *camelina* selected from a cross between accession 'A3U7761', a material originated in Austria, and 'Ames 1043', a material originated in Poland. A representative sample of seeds of 'SO-50' has been deposited under ATCC Accession No. PTA-11480 on Nov. 12, 2010.

Breeding Methods

Open-Pollinated Populations. The improvement of open-pollinated populations of such crops as rye, many maizes and sugar beets, herbage grasses, legumes such as alfalfa and clover, and tropical tree crops such as cacao, coconuts, oil palm and some rubber, depends essentially upon changing gene-frequencies towards fixation of favorable alleles while maintaining a high (but far from maximal) degree of heterozygosity. Uniformity in such populations is impossible and trueness-to-type in an open-pollinated variety is a statistical feature of the population as a whole, not a characteristic of individual plants. Thus, the heterogeneity of open-pollinated populations contrasts with the homogeneity (or virtually so) of inbred lines, clones and hybrids.

Population improvement methods fall naturally into two groups, those based on purely phenotypic selection, normally called mass selection, and those based on selection with progeny testing. Interpopulation improvement utilizes the concept of open breeding populations; allowing genes to flow from one population to another. Plants in one population (cultivar, strain, ecotype, or any germplasm source) are crossed either naturally (e.g., by wind) or by hand or by bees (commonly *Apis mellifera* L. or *Megachile rotundata* F.) with plants from other populations. Selection is applied to improve one (or sometimes both) population(s) by isolating plants with desirable traits from both sources.

There are several primary methods of open-pollinated population improvement. First, there is the situation in which a population is changed en masse by a chosen selection procedure. The outcome is an improved population that is indefinitely propagable by random-mating within itself in isolation. Second, the synthetic variety attains the same end result as population improvement but is not itself propagable as such; it has to be reconstructed from parental lines or clones. Third, a method used in plant species that are largely self-pollinated in nature, such as soybeans, wheat, rice, safflower, *camelina* and others is pedigree selection. In this situation, crosses are made and individual plants and lines from individual plants are selected for desired traits. These lines are then advanced as genetically homogeneous varieties. Since the individuals are largely self pollinated these lines are analogous to an inbred line with favorable agronomic characteristics. These plant breeding procedures for improving open-pollinated populations are well known to those skilled in the art and comprehensive reviews of breeding procedures routinely used for improving cross-pollinated plants are provided in numerous texts and articles, including: Allard, Principles of Plant Breeding, John Wiley & Sons, Inc. (1960); Simmonds, Principles of Crop Improvement, Longman Group Limited (1979); Hallauer and Miranda, Quantitative Genetics in Maize Breeding, Iowa State University Press (1981); and, Jensen, Plant Breeding Methodology, John Wiley & Sons, Inc. (1988).

Mass Selection. In mass selection, desirable individual plants are chosen, harvested, and the seed composited without progeny testing to produce the following generation. Since selection is based on the maternal parent only, and there is no control over pollination, mass selection amounts to a form of random mating with selection. As stated above, the purpose of mass selection is to increase the proportion of superior genotypes in the population.

Synthetics. A synthetic variety is produced by crossing inter se a number of genotypes selected for good combining ability in all possible hybrid combinations, with subsequent maintenance of the variety by open pollination. Whether parents are (more or less inbred) seed-propagated lines, as in some sugar beet and beans (Vicia) or clones, as in herbage grasses, clovers and alfalfa, makes no difference in principle. Parents are selected on general combining ability, sometimes by test crosses or topcrosses, more generally by polycrosses. Parental seed lines may be deliberately inbred (e.g. by selfing or sib crossing). However, even if the parents are not deliberately inbred, selection within lines during line maintenance will ensure that some inbreeding occurs. Clonal parents will, of course, remain unchanged and highly heterozygous.

Whether a synthetic can go straight from the parental seed production plot to the farmer or must first undergo one or two cycles of multiplication depends on seed production and the scale of demand for seed. In practice, grasses and clovers are generally multiplied once or twice and are thus considerably removed from the original synthetic.

While mass selection is sometimes used, progeny testing is generally preferred for polycrosses, because of their operational simplicity and obvious relevance to the objective, namely exploitation of general combining ability in a synthetic.

The number of parental lines or clones that enter a synthetic vary widely. In practice, numbers of parental lines range from 10 to several hundred, with 100-200 being the average.

Broad based synthetics formed from 100 or more clones would be expected to be more stable during seed multiplication than narrow based synthetics.

Pedigreed varieties. A pedigreed variety is a superior genotype developed from selection of individual plants out of a segregating population followed by propagation and seed increase of self pollinated offspring and careful testing of the genotype over several generations. This is an open pollinated method that works well with naturally self pollinating species. This method can be used in combination with mass selection in variety development. Variations in pedigree and mass selection in combination are the most common methods for generating varieties in self pollinated crops.

Hybrids. A hybrid is an individual plant resulting from a cross between parents of differing genotypes. Commercial hybrids are now used extensively in many crops, including corn (maize), sorghum, sugarbeet, sunflower and broccoli. Hybrids can be formed in a number of different ways, including by crossing two parents directly (single cross hybrids), by crossing a single cross hybrid with another parent (three-way or triple cross hybrids), or by crossing two different hybrids (four-way or double cross hybrids).

Strictly speaking, most individuals in an out breeding (i.e., open-pollinated) population are hybrids, but the term is usually reserved for cases in which the parents are individuals whose genomes are sufficiently distinct for them to be recognized as different species or subspecies. Hybrids may be fertile or sterile depending on qualitative and/or quantitative differences in the genomes of the two parents. Heterosis, or hybrid vigor, is usually associated with increased heterozygosity that results in increased vigor of growth, survival, and fertility of hybrids as compared with the parental lines that were used to form the hybrid. Maximum heterosis is usually achieved by crossing two genetically different, highly inbred lines.

The production of hybrids is a well-developed industry, involving the isolated production of both the parental lines and the hybrids which result from crossing those lines. For a detailed discussion of the hybrid production process, see, e.g., Wright, Commercial Hybrid Seed Production 8:161-176, In Hybridization of Crop Plants.

Additional breeding methods have been known to one of ordinary skill in the art, e.g., methods discussed in Chahal and Gosal (Principles and procedures of plant breeding: biotechnological and conventional approaches, CRC Press, 2002, ISBN 084931321X, 9780849313219), Taji et al. (In vitro plant breeding, Routledge, 2002, ISBN 156022908X, 9781560229087), Richards (Plant breeding systems, Taylor & Francis US, 1997, ISBN 0412574500, 9780412574504), Hayes (Methods of Plant Breeding, READ BOOKS, 2007, ISBN 1406737062, 9781406737066), and Lörz et al. (Molecular marker systems in plant breeding and crop improvement, Springer, 2005, ISBN 3540206892, 9783540206897), each of which is incorporated by reference in its entirety.

DEPOSIT INFORMATION

A deposit of the seed of *Camelina sativa* (L.) variety 'SO-50' is maintained by Sustainable Oils, LLC, Sustainable Oils, LLC, 214 Shepherd Trail, Suite F, Bozeman, Mont. 59718, USA. In addition, a sample of the seed of *Camelina sativa* (L.) variety 'SO-50' has been deposited by Sustainable Oils, LLC, with American Type Culture Collection (ATCC), 10801 University Blvd. Manassas, Va. 20110-2209, USA.

To satisfy the enablement requirements of 35 U.S.C. §112, and to certify that the deposit of the seeds of the present invention meets the criteria set forth in 37 C.F.R. §§1.801-1.809, Applicants hereby make the following statements regarding the deposited seed of *Camelina sativa* (L.) variety 'SO-50' (deposited as ATCC Accession No. PTA-11480 on Nov. 12, 2010):

1. During the pendency of this application, access to the invention will be afforded to the Commissioner upon request;
2. Upon granting of the patent the strain will be available to the public under conditions specified in 37 CFR 1.808;
3. The deposit will be maintained in a public repository for a period of 30 years or 5 years after the last request or for the enforceable life of the patent, whichever is longer;
4. The viability of the biological material at the time of deposit will be tested; and
5. The deposit will be replaced if it should ever become unavailable.

Access to this deposit will be available during the pendency of this application to persons determined by the Commissioner of Patents and Trademarks to be entitled thereto under 37 C.F.R. §1.14 and 35 U.S.C. §122. Upon allowance of any claims in this application, all restrictions on the availability to the public of the variety will be irrevocably removed by affording access to a deposit of at least 2,500 seeds of the same seed source with ATCC.

EXAMPLES

Testing of Seed Quality Traits

Oil Content Determination In *Camelina* Seeds

Determination of Oil Content-method based on a contiguous wave low-resolution Nuclear magnetic Resonance Spectrometry was used. Seed oil content was determined using a 20 MHz TD-NMR oil seed analyzer (Bruker Optics, Inc., The Woodlands, Tex., USA).

Fatty Acid Composition from the Oil Contained in the Seeds

A GLC method was adopted for fatty acid analysis, which was performed using a Shimadzu 2010 dual-FID gas chromatograph (Shimadzu Scientific Instruments, Columbia, Md., USA).

Overview of the Invention

The present invention is based on the development of true-bred *camelina* seeds with unique characteristics, including but nor limited to the followings:

When compared to check varieties, the plants of the invented variety are characterized by having a relatively higher number of racemes per plant (9, ranging from 6 to 12), they exhibit a pronounced main raceme length (318 mm, ranging from 206 mm to 396 mm), an pronounced inflorescence length (58 cm, ranging from 44 cm to 68 cm) and a reduced inflorescence diameter (18 cm, ranging from 11 cm to 52 cm). Also, they exhibit an increased number of pods per plant (245, range of 145 to 394), a slightly heavier pod weight (4.5 g, range of 2.6 g to 6.9 g), and average number of seeds per pod (8, range of 6 to 10), an increased number of seeds per plant (1989, ranging from 1081 to 3000), and an average seed weight (1.26 g/1000, ranging from 1.08 g/1000 to 1.48 g/1000) (Table 1).

In addition, the present invention involves in the development of true-bred *camelina* seeds capable of growing and providing adequate seed yields under low input, dryland conditions in the USA and having but not limited to the following characteristics:

(i) The plants of the invention mature 106 days after planting which is the period required by popular *camelina* varieties to reach maturity in areas where the invention is intended to be produced.

(ii) The plants of the invention provide a grain yield of 1746 Lbs/ac which is higher than those provided by plants from varieties currently grown in the area. Also, the levels of variation in grain yield in response to fluctuations in growing conditions is less in the plants from the invention compared to the levels of variation observed in other varieties currently grown in the area.

(iii) The invention produces a total of 1989 seeds per plant which is higher than the number of seeds per plant observed for materials currently grown in the area. Clearly, increased seed number can be considered the distinctive quality of this variety.

(iv) The plants of the invention produce an average total oil yield of 666 Lbs/ac, which is higher than those produced by plants from varieties currently grown in the area.

The following table compares selected plant characteristics of 'SO-50' as compared to the check variets 'Blaine Creek'.

TABLE 1

Variety description information[†]

| Variety | Minimum | Maximum | Mean | Standard deviation | Mean % compared to Blaine Creek |
|---|---|---|---|---|---|
| Raceme number | | | | | |
| SO-50 | 6 | 12 | 9 | 1.6 | 112.5% |
| Blaine Creek | 7 | 13 | 8 | 1.4 | 100% |
| Main raceme length (mm) | | | | | |
| SO-50 | 206 | 396 | 318 | 45.8 | 109.3% |
| Blaine Creek | 185 | 414 | 291 | 46.9 | 100% |
| Inflorescence length (cm) | | | | | |
| SO-50 | 44 | 68 | 58 | 5.5 | 116% |
| Blaine Creek | 25 | 67 | 50 | 8.6 | 100% |
| Inflorescence diameter (cm) | | | | | |
| SO-50 | 11 | 52 | 18 | 8.1 | 81.8% |
| Blaine Creek | 10 | 35 | 22 | 5.7 | 100% |
| Pod number | | | | | |
| SO-50 | 145 | 394 | 245 | 57 | 105.2% |
| Blaine Creek | 161 | 415 | 233 | 68.7 | 100% |
| Pod weight (g) | | | | | |
| SO-50 | 2.6 | 6.9 | 4.5 | 1.0 | 107.1% |
| Blaine Creek | 2.5 | 7.4 | 4.2 | 1.2 | 100% |
| Seeds per pod | | | | | |
| SO-50 | 6 | 10 | 8 | 1.2 | 100% |
| Blaine Creek | 6 | 13 | 8 | 1.6 | 100% |
| Seeds per plant | | | | | |
| SO-50 | 1081 | 3000 | 1989 | 474.6 | 106.6% |
| Blaine Creek | 1241 | 3016 | 1866 | 456.4 | 100% |
| Seed weight (g/1000) | | | | | |
| SO-50 | 1.08 | 1.48 | 1.26 | 0.09 | 100% |
| Blaine Creek | 1.08 | 1.46 | 1.26 | 0.10 | 100% |

[†]Data collected from 25 random mature plants grown under field conditions in Moccasin, MT.

Development of 'SO-50'

'SO-50' was derived from a cross between accession 'A3U7761', a material originated in Austria, and accession 'Ames 1043', a material originated in Poland. These accessions were evaluated for agronomic performance and adaptability across multiples sites during the period of 2006-2009 (Tables 2 and 3). A form of a modified bulk-pedigree selection scheme was used for its development (Table 4). A cross between 'A3U7761; and 'Ames 1043' was made in the spring season at a field nursery in Kalispell, Mont. During the winter the F1 hybrid seed was advanced at a greenhouse in Bozeman, Mont., and in the next spring season the F2 seed was grown in a selection nursery in Bozeman, Mont. in duplicated plots (100 ft² each). At maturity a total of 40 individual plants were selected and harvested from this population; selection criteria included early maturity, medium plant height, increased branch and pod number, and good overall appearance. A random portion of seed from each of these F3 families was collected and bulked, and during the next winter season this bulked seed was planted in a winter nursery near Yuma, Ariz. in duplicated plots (100 ft² each). At maturity at least 30 individual plants were selected and harvested from this population using the criteria described above and a random portion of seed from each plant was collected and bulked.

During the next spring season the bulked F4 seed from this population was planted in duplicated plots (100 ft² each) in a selection nursery near Bozeman, Mont., which also included 60 F4 breeding materials and 4 *Camelina* accessions used as checks. At maturity a number of individual plants were selected from each of these populations for future breeding work using the same criteria as before. After selections were made the remaining of the plots were harvested and grain was collected. These breeding populations were ranked based on grain yield performance and agronomic attributes, being the population derived from A3U7761/Ames 1043 among the top 20% of the group. In the following spring a random portion of the F5 seed derived from A3U7761/Ames 1043 was planted in an isolated field near Bozeman, Mont.

During the winter, a random sample of the collected F6 seed was increased in Chile, and in the next two springs and the intervening winter season the performance of 'SO-50' was evaluated in replicated field trials across a wide geographic region including Montana (Bozeman, Havre, and Moccasin), Arizona (Yuma), North Dakota (Carrington), Wyoming (Lingle), Washington (Dusty), and Oregon (Pendleton), USA (Table 5). Three locally grown cultivars, 'Calena', 'Blaine Creek', and 'SO-30', were also included in these trials and used as checks/controls for comparative purposes. These evaluations were carried out under standard production practices.

TABLE 2

Specifics on field evaluations of accessions 'A3U7761' and 'Ames 1043'

| Set | Entries | Year | Season | Site(s)[†] |
|---|---|---|---|---|
| 1 | 33 | 2006 | Spring | 8 |
| 2 | 45 | 2007 | Spring | 5 |
| 3 | 46 | 2007 | Spring | 2 |
| 4 | 12 | 2007 | Spring | 11 |
| 5 | 20 | 2007/2008 | Winter | 1 |
| 6 | 20 | 2008 | Spring | 25 |
| 7 | 20 | 2008 | Spring | 5 |
| 8 | 20 | 2008/2009 | Winter | 1 |
| 9 | 21 | 2009 | Spring | 7 |
| 10 | 46 | 2009 | Spring | 2 |
| 11 | 20 | 2009 | Spring | 16 |

[†]Sites covered representative areas in Arizona, AZ, Idaho, ID, Montana, MT North Dakota, ND, Nebraska, NE, New Mexico, NM, Oregon, OR, South Dakota, SD, Washington, WA, and Wyoming, WY, in the USA and in Alberta, AL, Manitoba, MB, and Saskatchewan, SK, in Canada.

TABLE 3

Agronomic performance of accessions 'A3U7761' and 'Ames 1043'

| Accession | Set 1 | Set 2 | Set 3 | Set 4 | Set 5 | Set 6 | Set 7 | Set 8 | Set 9 | Set 10 | Set 11 | Mean |
|---|---|---|---|---|---|---|---|---|---|---|---|---|
| Grain yield (Lbs/ac) | | | | | | | | | | | | |
| A3U7761 | 1408 | 1731 | 1941 | 1446 | 1728 | 1394 | 1868 | 1208 | 1725 | 2131 | 1720 | 1664 |
| Ames 1043 | 1385 | 1710 | — | 1381 | 1736 | 1381 | 1796 | 1192 | 1744 | — | 1579 | 1545 |
| Mean | 1256 | 1602 | 1673 | 1330 | 1389 | 1197 | 1695 | 926 | 1669 | 1912 | 1480 | 1466 |
| Seed weight (g/1000) | | | | | | | | | | | | |
| A3U7761 | 1.13 | 1.05 | 1.07 | 1.07 | 1.10 | 1.16 | 1.25 | 0.86 | 1.19 | — | 1.39 | 1.13 |
| Ames 1043 | 1.16 | 1.09 | — | 1.12 | 1.10 | 1.17 | 1.30 | 0.86 | 1.25 | — | 1.39 | 1.16 |
| Mean | 1.04 | 0.99 | 1.01 | 1.10 | 0.95 | 1.08 | 1.19 | 0.74 | 1.15 | — | 1.33 | 1.06 |
| Oil content (%) | | | | | | | | | | | | |
| A3U7761 | 37.12 | 37.08 | 33.52 | 35.28 | — | 34.35 | 36.16 | — | 39.03 | 41.41 | 39.59 | 37.06 |
| Ames 1043 | 37.50 | 36.22 | — | 34.97 | — | 34.25 | 36.40 | — | 39.14 | . | 39.65 | 36.88 |
| Mean | 36.90 | 35.75 | 33.40 | 34.89 | — | 33.84 | 36.21 | — | 38.64 | 40.36 | 38.63 | 36.51 |
| Oil yield (Lbs/ac) | | | | | | | | | | | | |
| A3U7761 | 529 | 634 | 632 | 502 | — | 490 | 674 | — | 679 | 764 | 687 | 621 |
| Ames 1043 | 512 | 606 | — | 483 | — | 492 | 643 | — | 686 | — | 631 | 579 |
| Mean | 465 | 560 | 552 | 464 | — | 414 | 618 | — | 649 | 720 | 579 | 558 |

TABLE 4

Breeding method used in the development of 'SO-50'

| Generation | Activity | Season | Location |
|---|---|---|---|
| F1 | Crosses | Spring | Kalispell, MT |
| F2 | Seed advance in greenhouse | Winter | Bozeman, MT |
| F3 | Sample of seed from each F2 plant bulked and planted in duplicated plots in a spring nursery. Single plant selections, selection criteria included early maturity, short plant stature, increased branching, increased pod number, good overall appearance | Spring | Bozeman, MT |
| F4 | Sample of seed from each F3 line bulked and planted in a winter nursery. Single plant selections, selection criteria included early maturity, short stature, increased branching, increased pod number, overall good appearance | Winter | Yuma, AZ |
| F5 | Sample of seed from each F4 line bulked and planted in duplicated plots in a spring nursery Population selected based on grain yield | Spring | Bozeman, MT |

TABLE 4-continued

Breeding method used in the development of 'SO-50'

| Generation | Activity | Season | Location |
|---|---|---|---|
| | performance and same attributes specified above | | |
| F6 | Seed increase and seed purification in isolation field | Spring | Bozeman, MT |
| | Multilocation yield evaluation trials Seed oil quality evaluations | | Bozeman, MT; Havre, MT Moccasin, MT |
| F7 | Seed increase Yield evaluation trial Seed oil quality evaluations | Winter | Chile Yuma, AZ |
| | Multilocation yield evaluation trials Seed oil quality evaluations | Spring | Bozeman, MT; Carrington, ND Dusty, WA; Havre, MT Lingle, WY; Moccasin, MT; Pendelton, OR |

TABLE 5

Specifics on field evaluations of 'SO-50'

| Site | Latitude and Longitude | Total seasonal water available[†] mm | Average monthly temperature[‡] °F. |
|---|---|---|---|
| Bozeman, MT, 2009 | 45° 47' N, 111° 20' W | 264 | 52 |
| Bozeman, MT, 2010 | 45° 41' N, 111° 13' W | 305 | 52 |
| Carrington, ND, 2010 | 47° 31' N, 99° 07' W | 427 | 55 |
| Dusty, WA, 2010 | 46° 47' N, 117° 41' W | 358 | 57 |
| Havre, MT, 2009 | 48° 29' N, 109° 48' W | 184 | 50 |
| Havre, MT, 2010 | 48° 29' N, 109° 48' W | 261 | 51 |
| Lingle, WY, 2010 | 42° 08' N, 104° 20' W | 358 | 57 |
| Moccasin, MT, 2009 | 47° 03' N, 109° 57' W | 288 | 48 |
| Moccasin, MT, 2010 | 47° 03' N, 109° 57' W | 363 | 49 |
| Pendleton, OR, 2010 | 45° 43' N, 118° 37' W | 304 | 56 |
| Yuma, AZ, 2009/2010 | 32° 34' N, 114° 42' W | 427 | 79 |

[†]Amount of water from seasonal precipitation (November previous year to July seasonal year) except for Bozeman, MT 2010 and Yuma, AZ 2009/2010 where water from irrigation equivalent to 15 mm and 337 mm of water, respectively, was applied.
[‡]Average monthly temperature for the period March-July.

The invented variety reaches 50% flowering at 67 days after planting (range of 56 and 87 days after planting) and matures 106 days after planting (range of 103 to 109 days after planting), phenological periods that are very similar to those observed for 'Galena', 'Blaine Creek' and "SO-30" (Tables 6 and 7).

TABLE 6

Days to 50% flowering of 'SO-50' and popular *camelina* varieties

| Variety | Bozeman 2009 | Havre 2009 | Yuma 2009 | Bozeman 2010 | Dusty 2010 | Havre 2010 | Lingle 2010 | Average | Mean % compared to Blaine Creek |
|---|---|---|---|---|---|---|---|---|---|
| SO-50 | 56 | 67 | 87 | 56 | 73 | 66 | 66 | 67 | 100% |
| Calena | 55 | 67 | 87 | 56 | 74 | 66 | 67 | 67 | 100% |
| Blaine Creek | 55 | 66 | 86 | 55 | 73 | 65 | 66 | 67 | 100% |
| SO-30 | 55 | 67 | 87 | 56 | 73 | 69 | 68 | 68 | 101.5% |

TABLE 7

Days to maturity of 'SO-50' and popular *camelina* varieties

| Variety | Bozeman 2009 | Havre 2009 | Dusty 2010 | Havre 2010 | Average | Mean % compared to Blaine Creek |
|---|---|---|---|---|---|---|
| SO-50 | 105 | 103 | 109 | 105 | 106 | 100.9% |
| Calena | 104 | 103 | 110 | 104 | 105 | 100% |
| Blaine Creek | 105 | 102 | 110 | 103 | 105 | 100% |
| SO-30 | 104 | 103 | 111 | 107 | 106 | 100.9% |

'SO-50' produces an average grain yield of 1746 Lbs/ac (1059 Lbs/ac to 2542 Lbs/ac), which is higher than the average yields produced by the control varieties (1657 Lbs/ac, 1635 Lbs/ac, and 1679 Lbs/ac for 'Calena', 'Blaine Creek' and "SO-30", respectively (Table 8)). In addition, the variation of grain yield in response to environmental fluctuations, measured by the standard deviation across environments, is small in 'SO-50' relative to the control varieties. Consistent with these observations, 'SO-50' can be considered a high yielding, highly stable variety.

TABLE 8

Grain yield (Lbs/ac) of 'SO-50' and popular *camelina* varieties

| Variety | Bozeman 2009 | Havre 2009 | Moccasin 2009 | Yuma 2009 | Bozeman 2010 | Carrington 2010 | Dusty 2010 | Havre 2010 | Moccasin 2010 | Lingle 2010 | Pendleton 2010 | Average | SD | Mean % compared to Blaine Creek |
|---|---|---|---|---|---|---|---|---|---|---|---|---|---|---|
| SO-50 | 2542 | 2037 | 1722 | 1381 | 1261 | 2179 | 1059 | 2157 | 1920 | 1478 | 1474 | 1746 | 457 | 106.8% |
| Calena | 2508 | 1960 | 1713 | 1476 | 859 | 1926 | 987 | 2011 | 1956 | 1439 | 1392 | 1657 | 484 | 101.3% |
| Blaine Creek | 2495 | 2048 | 1388 | 1282 | 852 | 2046 | 960 | 1992 | 1792 | 1497 | 1639 | 1635 | 501 | 100% |
| SO-30 | 2559 | 1902 | 1718 | 1308 | 1077 | 2077 | 952 | 2145 | 1947 | 1324 | 1457 | 1679 | 498 | 102.7% |

In regard to other agronomic characteristics, 'SO-50' has an average height of 33 inches (ranging from 29 to 40 inches) which is very similar to that observed in the each of the controls (Table 9). Thus, 'SO-50' can be considered a mid-size variety.

TABLE 9

Plant height (inches) of 'SO-50' and popular *camelina* varieties

| Variety | Bozeman 2009 | Havre 2009 | Moccasin 2009 | Carrington 2010 | Dusty 2010 | Havre 2010 | Lingle 2010 | Moccasin 2010 | Average | Mean % compared to Blaine Creek |
|---|---|---|---|---|---|---|---|---|---|---|
| SO-50 | 35 | 32 | 29 | 31 | 31 | 37 | 29 | 40 | 33 | 103.1% |
| Calena | 35 | 33 | 29 | 31 | 32 | 35 | 28 | 41 | 33 | 103.1% |
| Blaine Creek | 34 | 32 | 28 | 31 | 31 | 34 | 29 | 40 | 32 | 100% |
| SO-30 | 36 | 33 | 26 | 31 | 32 | 36 | 30 | 41 | 33 | 103.1% |

The average seed filling period is 40 days (ranging from 36 to 49 days) which is the same as that observed for the control materials (Table 10).

TABLE 10

Seed filling (days) of 'SO-50' and popular *camelina* varieties

| Variety | Bozeman 2009 | Havre 2009 | Dusty 2010 | Havre 2010 | Average | Mean % compared to Blaine Creek |
|---|---|---|---|---|---|---|
| SO-50 | 49 | 37 | 36 | 39 | 40 | 100% |
| Calena | 50 | 36 | 37 | 38 | 40 | 100% |
| Blaine Creek | 50 | 36 | 37 | 37 | 40 | 100% |
| SO-30 | 49 | 36 | 38 | 39 | 40 | 100% |

'SO-50' produces seed that have an average weight of 1.30 g/1000 which is slightly higher than that observed for the control materials (ranging from 1.23 to 1.29 g/1000) (Table 11).

Average test weight is 53.3 Lbs/Bu (with a range of 52.3 Lbs/Bu to 55.1 Lbs/Bu) which is very similar to those observed in the control varieties (ranging from 52.8 Lbs/Bu to 53.4 Lbs/Bu) (Table 12).

In relation to oil quality attributes, the average amount of oil contained in the seeds of 'SO-50' corresponds to 37.56% (range of 33.46% to 41.20%) which is very similar to the average amount observed in the seeds of the control varieties (36.86% to 37.49%) (Table 13).

SO-50' produces an average oil yield of 666 Lbs/ac (range of 375 Lbs/ac to 1074 Lb/ac) which is higher than the average amount produced by the control varieties (range of 611 Lbs/ac to 625 Lbs/ac) (Table 14), thus it can be considered a highly oil productive variety.

The seeds of the invented variety exhibit a fatty acid profile that is very similar to that observed in the seeds of the control varieties (Table 15).

TABLE 11

Seed weight (g/1000) of 'SO-50' and popular *camelina* varieties

| Variety | Bozeman 2009 | Havre 2009 | Moccasin 2009 | Bozeman 2010 | Carrington 2010 | Dusty 2010 | Lingle 2010 | Moccasin 2010 | Pendleton 2010 | Average | Mean % compared to Blaine Creek |
|---|---|---|---|---|---|---|---|---|---|---|---|
| SO-50 | 1.32 | 1.28 | 1.05 | 1.39 | 1.50 | 1.31 | 1.33 | 1.35 | 1.24 | 1.30 | 105.7% |
| Calena | 1.29 | 1.23 | 1.03 | 1.33 | 1.44 | 1.23 | 1.37 | 1.28 | 1.23 | 1.27 | 103.3% |
| Blaine Creek | 1.26 | 1.21 | 0.95 | 1.32 | 1.37 | 1.19 | 1.30 | 1.27 | 1.19 | 1.23 | 100% |
| SO-30 | 1.27 | 1.28 | 1.10 | 1.37 | 1.49 | 1.28 | 1.31 | 1.23 | 1.25 | 1.29 | 104.9% |

TABLE 12

Test weight (Lbs/Bu) of 'SO-50' and popular *camelina* varieties

| Variety | Bozeman 2009 | Havre 2009 | Moccasin 2009 | Yuma 2009 | Bozeman 2010 | Carrington 2010 | Havre 2010 | Moccasin 2010 | Average | Mean % compared to Blaine Creek |
|---|---|---|---|---|---|---|---|---|---|---|
| SO-50 | 53.9 | 52.6 | 52.4 | 55.1 | 53.7 | 53.2 | 52.3 | 52.8 | 53.3 | 100.9% |
| Calena | 52.6 | 52.6 | 51.9 | 55.0 | 53.6 | 52.4 | 52.6 | 52.5 | 52.9 | 100.2% |
| Blaine Creek | 52.8 | 52.1 | 51.9 | 54.9 | 53.3 | 52.6 | 52.6 | 52.7 | 52.8 | 100% |
| SO-30 | 53.8 | 52.7 | 52.7 | 55.7 | 53.6 | 53.0 | 52.5 | 53.0 | 53.4 | 101.1% |

TABLE 13

Seed oil content (%) of 'SO-50' and popular *camelina* varieties

| Variety | Bozeman 2009 | Havre 2009 | Moccasin 2009 | Yuma 2009 | Bozeman 2010 | Carrington 2010 | Dusty 2010 | Moccasin 2010 | Lingle 2010 | Pendleton 2010 | Average | Mean % compared to Blaine Creek |
|---|---|---|---|---|---|---|---|---|---|---|---|---|
| SO-50 | 41.20 | 40.54 | 34.84 | 36.46 | 39.98 | 39.39 | 35.40 | 37.52 | 33.46 | 36.79 | 37.56 | 100.2% |
| Calena | 40.97 | 39.79 | 33.52 | 36.56 | 39.81 | 38.98 | 33.65 | 36.95 | 31.84 | 36.56 | 36.86 | 98.3% |
| Blaine Creek | 40.85 | 39.89 | 34.44 | 36.45 | 40.37 | 38.58 | 36.83 | 38.32 | 33.00 | 36.15 | 37.49 | 100% |
| SO-30 | 40.30 | 40.00 | 35.08 | 35.98 | 39.02 | 38.34 | 37.25 | 36.05 | 32.82 | 36.19 | 37.10 | 99.0% |

TABLE 14

Seed oil yield (Lbs/ac) of 'SO-50' and popular *camelina* varieties

| Variety | Bozeman 2009 | Havre 2009 | Moccasin 2009 | Bozeman 2010 | Carrington 2010 | Dusty 2010 | Lingle 2010 | Moccasin 2010 | Pendleton 2010 | Average | Mean % compared to Blaine Creek |
|---|---|---|---|---|---|---|---|---|---|---|---|
| SO-50 | 1074 | 826 | 600 | 504 | 857 | 375 | 494 | 719 | 542 | 666 | 107.6% |
| Calena | 1027 | 779 | 577 | 341 | 751 | 331 | 459 | 723 | 509 | 611 | 98.7% |

TABLE 14-continued

Seed oil yield (Lbs/ac) of 'SO-50' and popular camelina varieties

| Variety | Bozeman 2009 | Havre 2009 | Moccasin 2009 | Bozeman 2010 | Carrington 2010 | Dusty 2010 | Lingle 2010 | Moccasin 2010 | Pendleton 2010 | Average | Mean % compared to Blaine Creek |
|---|---|---|---|---|---|---|---|---|---|---|---|
| Blaine Creek | 1020 | 816 | 478 | 344 | 789 | 353 | 494 | 687 | 592 | 619 | 100% |
| SO-30 | 1031 | 760 | 603 | 420 | 795 | 354 | 436 | 701 | 527 | 625 | 101.0% |

TABLE 15

Fatty acid composition from seed oil (%) of 'SO-50' and popular camelina varieties

| Variety | Palmitic (C16:0) | % compared to Blaine Creek | Oleic (C18:1) | % compared to Blaine Creek | Linoleic (C18:2) | % compared to Blaine Creek | Linolenic (C18:3) | % compared to Blaine Creek | Eicosenoic (C20:1) | % compared to Blaine Creek | Erucic (C22:1) | % compared to Blaine Creek |
|---|---|---|---|---|---|---|---|---|---|---|---|---|
| SO-50 | 5.98 | 99.2% | 16.50 | 94.5% | 19.57 | 102.8% | 35.94 | 101.1% | 13.74 | 98.1% | 0.17 | 130.8% |
| Calena | 6.06 | 100.5% | 15.66 | 89.7% | 19.11 | 100.4% | 36.91 | 103.9% | 13.72 | 97.9% | 0.14 | 107.7% |
| Blaine Creek | 6.03 | 100% | 17.45 | 100% | 19.03 | 100% | 35.54 | 100% | 14.01 | 100% | 0.13 | 100% |
| SO-30 | 6.27 | 104.0% | 15.53 | 89.0% | 21.96 | 115.4% | 34.85 | 98.1% | 13.06 | 93.2% | 0.17 | 130.7% |

In view of the many possible embodiments to which the principles of the disclosed invention may be applied, it should be recognized that the illustrated embodiments are only examples and should not be taken as limiting the scope of the invention.

Unless defined otherwise, all technical and scientific terms herein have the same meaning as commonly understood by one of ordinary skill in the art to which this invention belongs.

All publications, patents, and patent publications cited are incorporated by reference herein in their entirety for all purposes.

The publications discussed herein are provided solely for their disclosure prior to the filing date of the present application. Nothing herein is to be construed as an admission that the present invention is not entitled to antedate such publication by virtue of prior invention.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth and as follows in the scope of the appended claims.

REFERENCES CITED

Anonymous. 2009. 14 Airlines sign landmark MOU for Camelina-based renewable jet fuel & green diesel, Dec. 15, 2009. Business Wire.

Bouby, L. 1998. Two early finds of gold-of-pleasure (Camelina sp.) in middle Neolithic and Chacolithic sites in western France. Antiquity, 72: 391-398.

Budin, J. T., W. M. Breene and D. H. Putnam, 1995. Some compositional properties of Camelina (Camelina sativa (L.) Crantz) seeds and oils. Journal of the American Oil Chemists Society, 72: 309-315.

Gugel, R. K. and K. C. Falk. Agronomic and seed quality evaluation of Camelina sativa in western Canada. 2006. Canadian Journal of Plant Science, 86:1047-1058.

Public Law 110-140. Energy Independence and Security Act of 2007.

Schultze-Motel, J., 1979. Die Anbaugeschichte des Leindotters, Camelina sativa (L.) Crantz.

Putnam, D. H., J. T. Budin, L. A. Field, and W. M. Breene. 1993. Camelina: A promising low-input oilseed. p. 314-322. In J. Janick, and J. E. Simon (eds), New Crops, Exploration, Research and Commercialization, John Wiley and Sons, Inc. New York, USA.

Robinson, R. G. 1987. Camelina: a useful research crop and a potential oilseed crop. University of Minnesota Agric. Exp. Stn. Bull. 579-1987 (Item No. AD-SB-3275), pp. 1-12.

Shonnard, D. R., L. Williams; and T. N. Kalnesc. 2010. Camelina-Derived Jet Fuel and Diesel: Sustainable Advanced Biofuels. Environmental Progress & Sustainable Energy, 29:382-392.

Vollmann, J., A. Damboeck, A. Eckl, H. Schrems, and P. Ruckenbauer. 1996. Improvement of Camelina sativa, an underexploited oilseed. p. 357-362. In: J. Janick (ed.), Progress in new crops. ASHS Press, Alexandria, Va.

The invention claimed is:

1. A seed of *Camelina sativa* (L.) variety designated 'SO-50', wherein a representative sample of seed of said variety has been deposited under ATCC Accession No. PTA-11480.

2. A *Camelina sativa* (L.) plant, or a part thereof, produced by growing the seed of claim 1.

3. A *Camelina sativa* (L.) plant, or a part thereof, having the physiological and morphological characteristics of *Camelina sativa* (L.) variety 'SO-50', wherein a representative sample of seed of said variety has been deposited under ATCC Accession No. PTA-11480.

4. A tissue culture of regenerable cells produced from the plant or plant part of claim 2.

5. The tissue culture of claim 4, wherein said cells of the tissue culture are produced from a plant part selected from the group consisting of embryos, meristematic cells, leaves, pollen, root, root tips, stems, anther, pistils, pods, flowers, and seeds.

6. A *Camelina sativa* (L.) plant regenerated from the tissue culture of claim 5, said plant having the morphological and physiological characteristics of *Camelina sativa* (L.) variety 'SO-50', wherein a representative sample of seed has been deposited under ATCC Accession No. PTA-11480.

7. A method for producing a *Camelina* seed comprising crossing a first parent *Camelina* plant with a second parent *Camelina* plant and harvesting the resultant hybrid bean seed, wherein said first parent *Camelina* plant or second parent *Camelina* plant is the *Camelina sativa* (L.) plant of claim 2.

8. A hybrid *Camelina* seed produced by the method of claim 7.

9. A method for producing an herbicide resistant *Camelina* plant comprising transforming the *Camelina sativa* (L.) plant of claim 2 with a transgene that confers herbicide resistance to an herbicide selected from the group consisting of imidazolinone, sulfonylurea, glyphosate, glufosinate, L-phosphinothricin, triazine, and benzonitrile.

10. An herbicide resistant *Camelina* plant, or a part thereof, produced by the method of claim 9.

11. A method for producing an insect resistant *Camelina* plant comprising transforming the *Camelina sativa* (L.) plant of claim 2 with a transgene that confers insect resistance.

12. An insect resistant *Camelina* plant, or a part thereof, produced by the method of claim 11.

13. A method for producing a disease resistant *Camelina* plant comprising transforming the *Camelina sativa* (L.) plant of claim 2 with a transgene that confers disease resistance.

14. A disease resistant *Camelina* plant, or a part thereof, produced by the method of claim 13.

15. A method of introducing a desired trait into *Camelina sativa* (L.) variety 'SO-50' comprising:
(a) crossing a *Camelina sativa* (L.) variety 'SO-50' plant grown from *Camelina sativa* (L.) variety 'SO-50' seed, wherein a representative sample of seed has been deposited under ATCC Accession No. PTA-11480, with another *Camelina* plant that comprises a desired trait to produce F1 progeny plants;
(b) selecting one or more progeny plants that have the desired trait to produce selected progeny plants;
(c) crossing the selected progeny plants with the *Camelina saliva* (L.) variety 'SO-50' plants to produce backcross progeny plants;
(d) selecting for backcross progeny plants that have the desired trait and physiological and morphological characteristics of *Camelina saliva* (L.) variety 'SO-50' to produce selected backcross progeny plants; and
(e) repeating steps (c) and (d) three or more times in succession to produce selected fourth or higher backcross progeny plants that comprise the desired trait and the physiological and morphological characteristics of *Camelina saliva* (L.) variety 'SO-50'.

16. A *Camelina* plant produced by the method of claim 15, wherein the plant has the desired trait and the physiological and morphological characteristics of *Camelina saliva* (L.) variety 'SO-50'.

17. A method for producing *Camelina saliva* (L.) variety 'SO-50' seed comprising crossing a first parent *Camelina saliva* (L.) plant with a second parent *Camelina saliva* (L.) plant and harvesting the resultant *Camelina saliva* (L.) seed, wherein both said first and second *Camelina saliva* (L.) plants are the *Camelina saliva* (L.) plant of claim 4.

18. The *Camelina* plant of claim 16, wherein the desired trait is herbicide resistance and the resistance is conferred to an herbicide selected from the group consisting of imidazolinone, sulfonylurea, glyphosate, glufosinate, L-phosphinothricin, triazine, and benzonitrile.

19. The *Camelina* plant of claim 16, wherein the desired trait is insect resistance and the insect resistance is conferred by a transgene encoding a *Bacillus thuringiensis* endotoxin.

20. The *Camelina* plant of claim 16, wherein the desired trait is selected from the group consisting of insect resistance, disease resistance, water stress tolerance, heat tolerance, improved shelf life, and improved nutritional quality.

* * * * *